United States Patent [19]

Chang et al.

[11] Patent Number: 4,526,980
[45] Date of Patent: Jul. 2, 1985

[54] METHOD FOR THE PREPARATION OF TETRANITRODIBENZOTETRAZAPENTALENE

[75] Inventors: Marguarite S. Chang, Oxon Hill; Robert R. Orndoff, Waldorf, both of Md.

[73] Assignee: The United States of America as represented by the Secretary of the Navy, Washington, D.C.

[21] Appl. No.: 511,366

[22] Filed: Jul. 6, 1983

[51] Int. Cl.$^3$ .................................... C07D 257/10
[52] U.S. Cl. .................................... 548/258
[58] Field of Search .................................... 548/258

[56] References Cited

U.S. PATENT DOCUMENTS 2,984,544  5/1961  Carboni .
3,184,472  5/1965  Carboni .................................... 548/258
3,197,475  7/1965  Carboni .

OTHER PUBLICATIONS

Barton and Ollis, *Comprehensive Organic Chemistry*, II, Perganon, New York, (1979), vol. 2, pp. 166–167.
Meislich, et al, *Schawn's Outline of Organic Chemistry*, McGraw-Hill, New York (1977), p. 295.
Carboni, et al., "Aromatic Azapentalenes I, . . . ", J. Am. Chem.-Soc. 89:11 pp. 2618-2625.
Theilheimer, *Synthetic Methods in Organic Chemistry*, vol. 14, (1960), No. 170.
Onote, et al., "Oxidation of Phenylendiamine . . . ", *Chem. Abst.* 75:118053a, (1971).
Carboni et al, JACS 89 p. 2618, (1967).
J. Macromol Sci. Chem., A7(8), pp. 1727-1749, (1973).

*Primary Examiner*—Donald G. Daus
*Assistant Examiner*—G. Hendricks
*Attorney, Agent, or Firm*—R. F. Beers; T. E. McDonnell

[57] ABSTRACT

Tetranitrodibenzo-1,3a,4,6a-tetrazapentalene is prepared from diaminobenzene by reacting diaminobenzene and lead dioxide in ethylacetate to produce diaminoazobenzene, isolating the product by silica-gel elution, reacting diaminoazobenzene with an inorganic azide in a dilute aqueous nitrous acid solution at a temperature not in excess of 10° C. to produce diazidoazobenzene, isolating the product, heating diazidoazobenzene slowly to about 190° C. until nitrogen stops evolving to form dibenzotetrazapentalene, isolating the product, nitrating dibenzotetrazapentalene with concentrated sulfuric acid and forming nitric at a temperature not in excess of about 65° C. to product tetranitrodibenzo-1,3a,4,6a-tetrazapentalene.

6 Claims, No Drawings

METHOD FOR THE PREPARATION OF TETRANITRODIBENZOTETRAZAPENTALENE

BACKGROUND OF THE INVENTION

The present invention pertains generally to organic energetic material synthesis and in particular to the synthesis of nitrated aromatic aza-compounds from diaminobenzene.

One nitrated aromatic aza-compound that has exceptional thermal stability and high energy content is tetranitrodibenzo-1,3a,4,6a-tetrazapentalene. This compound is used as a primer for energetic gas-producing devices, especially for cartridges used in cartridge-activated devices, e.g. canopy-release for fighter aircraft.

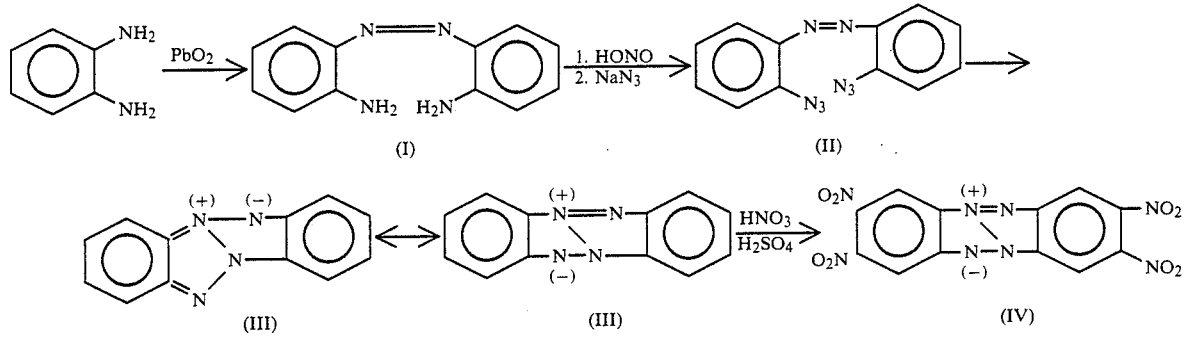

Presently the use of this compound has been restricted on account of the high cost. The compound is usually prepared by nitrating dibenzo-1,3a,4,6a-tetrazapentalene which is prepared by the method disclosed in U.S. Pat. No. 2,984,544, now U.S. Pat. No. Re. 25,238 and in U.S. Pat. No. 3,197,475 by Rudolf A. Carboni. Dibenzotetrazapentalene is prepared by the steps comprising oxidizing diaminoazobenzene to diazidoazobeneze by sodium azide and nitrous acid, and thermally cracking the azide substituents of diazidoazobenzene to form dibenzotetrazapentalene.

The diaminoazobenzene synthesis is disclosed in Carboni et al. *JACS* 89 p. 2618 (1967). By this method oxidation is carried out in benzene and product purification or isolation is achieved by extraction with methylene chloride. These two techniques contribute much to the high cost of the final product in that the reaction proceeds slowly, the yields are low, the purification is extremely slow, and the use of benzene requires many safety precautions.

SUMMARY OF THE INVENTION

It is, therefore, an object of the present invention to synthesize tetranitrodibenzo-tetrazapentalene from diaminobenzene without the use of benzene.

Another object of this invention is to prepare tetranitrodibenzo tetrazapentalene with simplified purification procedures.

A further object of the invention is to increase the yield and decrease the synthesis time for the preparation of tetranitrodibenzotetrazapentalene.

These and other objects are achieved by oxidizing diaminobenzene with lead oxide in ethyl acetate to obtain diaminoazobenzene, purifying diaminoazobenze by extraction in methylene chloride through silica gel, diazidoing diaminoazobenzene by oxiding with nitrous acid followed by slowly reacting with sodium azide under high-shear mixing, slowly heating the diazide product to a temperature from about 170° to about 185° C. to form dibenzotetrazapentalene, and nitrating dibenzotetrazapentalene by mixing therewith concentrated sulfuric acid under high-shear mixing following by a slow addition fuming nitric acid at a temperature from about −7° to about 0° C., followed by a rapid heating to a temperature from about 50° to 65° C. to quickly produce the tetra nitro product.

DETAILED DESCRIPTION OF THE INVENTION

The synthesis of the present invention proceeds in several stages, i.e. through several intermediate products. The principal synthesis steps are represented by the formulae:

The first intermediate is diaminoazobenzene DAAB which is prepared by forming a suspension of o-phenylenediamine in ethylacetate, admixing therewith an approximately stoichiometric amount of lead dioxide, and refluxing until the reaction is complete. The suspension is a dark color. The insoluble lead salts are easily separated by filtration, leaving a deep red orange filtrate. Purification of diaminoazobenzene proceeds by evaporating the filtrate to dryness, dissolving the filtrate in preferably methylene chloride, eluting the solution on silica gel (at least nine grams of silica gel per gram of solution and preferably from 10 to 15 grams of silica gel per gram of solution, collecting the red fraction, and drying the fraction. Additional details of the purification technique is found in Chang et al. *Functionality Distribution of Carboxyl- and Hydroxyl-Terminated Polybutadiene* J. Macromol. Sci.-Chem A7(8), p. 1727–49 (1973).

The reaction forming diaminoazobenzene also forms the double azo compound and polymers. The use of ethyl acetate is most preferred because it allows the reaction to proceed at a relatively fast rate and high yield at a temperature that minimizes double azoing and polymerizing, and has few safety problems. Fluids, such as methylene chloride, cyclohexane, and tetrahydrofuran can produce a yield, but it is too low to significantly reduce the high cost of the end product. The reaction must be run at a temperature from about 20° C. to about 100° C. Thus solvents with a boiling point below 20° C. can not be used.

Diaminoazobenzene is reacted to O,O'-diazidoazobenzene by the prior art method with the one exception of high-shear mixing the reaction. By high-shear mixing, reference is made to mixers operating at least 4000 RPM to produce turbulent conditions in the fluid being mixed. An example of a high-shear mixer is the mixer by the Premier Mill Corporation that is marked as the Disperoator and uses a duplex head. The synthesis comprises the steps of forming a suspension of diaminoazobenzene, concentrated hydrochloric acid or sulfuric acid, and water at a temperature from about −5° to 5° C. under high-shear agitation, slowly admixing therewith sodium or potassium nitrate to form nitrous acid, slowly admixing therewith an aqueous solution of sodium azide at a temperature from about 05° to about 10° C., and continuing to high-shear mix until the reaction mixture reaches room temperature. The rate of addition of sodium azide, the temperature, and the high-shear mixing controls the evolution of nitrogen to an acceptable level. Nitrous acid can be used directly, but would present safety and corrosion problems. Instead of sodium azide, lithium or potassium azide can be used, but these azides are dangerous and much more expensive. The amount of water to be used is not critical but enough to keep the reaction mixture fluid.

The diazide precipitates as yellow crystals, which are isolated in high purity by a simple filtration. Of course other separation techniques used to separate precipitates can be used.

Dibenzo-1,3a,4,6a-tetrazapentalene is prepared by the steps comprising forming a suspension of diazide in decalin, heating the suspension to about 58° C., whereupon nitrogen begins to evolve, slowly increasing the temperature at a rate of about 0.5 to about 2 degrees per minute to a temperature from about 160° C. to about 190° C., preferably from 175° to 185° C., and continue heating until nitrogen ceases evolving.

Again the product can be easily isolated by filtration. Purity can be increased by recrystalizing the tetrazapentalene from cyclohexane. Other solvents, e.g. benzene, can be used but are not preferred on account of safety or cost.

Nitration of the tetrazapentalene is difficult. The nitration method of this invention comprises slowly adding a suspension of dibenzotetrazapentalene and an concentrated solution of sulfuric acid to fuming nitric acid at a temperature from about −5° C. to about 5° C., and heating the reaction mixture to a temperature from about 55° to about 65° C. until the reaction is complete. The fuming nitric acid comprises concentrated nitric acid with dissolved nitrogen oxides. The amount of fuming acid is at least 25 weight percent of stoichiometry and preferably from 35 to 75 weight percent above stoichiometry. The amount of the sulfuric acid is the amount needed to dissolve pentalene compound. The concentration of the sulfuric acid is from about 80 to about 100 percent and preferably from 90 to 100 percent.

The preferred separation method comprises pouring the reaction mixture in ice water to precipitate the tetra nitro compound, filtering, and recrystalizing from dimethyl formamide. The final purity is in excess of 99.9 percent.

To further illustrate the practice of the present invention the following example is given. It is understood that the example is given by way of illustration and is not meant to limit this disclosure or the claims to follow in any manner.

EXAMPLE

A. Preparation of O,O′-Diaminoazobenzene (Solvent-Ethyl Acetate) (I)

To a stirred mixture of 4.5 g (0.05 mole) of O-phenylenediamine and 200 ml of ethyl acetate was added 23.9 g (0.1 mole) of lead dioxide. The mixture was immediately heated to reflux for 2 hours. The insoluble lead salts were removed by filtration and the deep red orange filtrate was evaporated to dryness. The solid, was dissolved in methylene chloride and eluted on a silica gel column (10 g silica gel/g sample) with methylene chloride. Collecting the red fraction, and evaporating the methylene chloride to dryness gave 4 g (98% yield) of DAAB with mp 133°–134°.

| Anal. calcd. for $C_{12}H_{12}N_4$: | C | 67.92 | Found | C | 67.86 |
|---|---|---|---|---|---|
| | H | 5.66 | | H | 5.68 |
| | N | 26.42 | | N | 26.45 |

A′. Preparation of O,O′-Diaminoazobenzene (Solvent-1. tetrahydrofuran, 2. cyclohexane, 3. methylene chloride)

The above procedure was repeated for each of the above solvents. Cyclohexane gave a 11 percent yield of low purity after about two hours of refluxing tetrahydrofuran gave a 24 percent yield of low purity after about three to four hours of refluxing. Methylene chloride gave an 80 percent yield with a 90 percent purity after four hours of refluxing.

B. Preparation of O′O′-Diazidoazobenzene (II)

A solution of 3.5 g (0.05 mole) of sodium nitrite in 20 ml of water was added dropwise to a stirred mixture of 4.3 g (0.02 mole) of DAAB, 30 ml of concentrated hydrochloric acid, and 40 ml of water at 0°–2° C. The temperature was maintained below 5° during the addition, stirring was continued for an additional ½ hour after the nitrite addition. Sodium azide (3.25 g, 0.05 mole) in 20 ml of water was slowly added to the diazonium solution at 0°–5° C. with continued vigorous stirring. Nitrogen evolved, and the yellow diazide precipitated during the addition. The mixture was stirred for an additional 2 hours (or until reaches to room temperature), then filtered to obtain the diazidoazobenzene (4.9 g) mp 100°–111° C.

C. Preparation of Dibenzo-1,3a,4,6a-Tetrazapentalene (III)

A suspension of 100 g of O,O′-diazidoazobenzene in 100 ml decalin in a 3000 ml three-neck flask was slowly heated to 175°–185° C. One mole of nitrogen evolved at 58° C.; the second mole of nitrogen evolved at 160° C. The suspension was continued to be heated at 175°–185° C. for three hours, cooled, and then filtered to obtain (III). It was recrystallized from cyclohexane or benzene. The yellow solid melted at 236°–237° C., the yield was 60 g.

| Anal. Calcd. for $C_{12}H_8N_4$ | C | 69.22 | Found | C | 69.28 |
|---|---|---|---|---|---|
| | H | 3.87 | | H | 3.95 |
| | N | 26.91 | | N | 26.82 |

D. Preparation of Tetranitrodibenzo-1,3a,4,6a-Tetrazapentalene (IV)

A 1.0 g sample of dibenzotetrazapentalene in 10 ml of concentrated sulfuric acid was added dropwise under stirring to 15 ml of fuming nitric acid which had been cooled to 5° C. After the addition was completed, the mixture was heated to 60° C. for 5 minutes, and then poured into ice water. A orange red solid was separated and collected by filtration and dried to give 1.4 g of the (IV) which can be recrystallized from dimethyl formamide. Melting point above 360° C.

| Anal. Calcd. for $C_{12}H_4N_8O_8$ | Found (crude sample) | Found (recrystallized sample) |
|---|---|---|
| C 37.11 | C 37.01; 37.00 | C 36.95; 37.19 |
| H 1.03 | H 0.92; 0.96 | H 0.97; 0.95 |
| N 28.87 | N 28.61; 28.75 | N 28.59; 28.61 |

Preliminary estimates of the cost of tetranitrodibenzo-1,3a,4,6a-tetrazapentalene show the cost of this material by the subject method to be one twentieth to one thirtieth of the commercial cost of this material. The synthesis time has been decreased by a factor of 3 to 5 by this method. The nitration technique of the subject synthesis yields the tetranitro product in a high yield. By this technique a large portion of dibenzotetrazapentalene is nitrated to the tetranitro product rather than the more readily produced trinitro product without decomposing the starting material.

Obviously, many modifications and variations of the present invention are possible in light of the above teachings. It is therefore to be understood that, within the scope of the appended claims, the invention may be practiced otherwise than as specifically described.

What is claimed is:

1. A method for preparing tetranitrodibenzo-1,3a,4,6a-tetrazapentalene which comprises:
    refluxing stoichiometric amounts of o-diaminobenzene and lead dioxide in ethyl acetate to form diaminoazobenzene;
    isolating diaminoazobenzene;
    forming a turbulent suspension of diaminoazobenzene, a concentrated acid selected from the group consisting of hydrochloric acid and sulfuric acid, and water at a temperature from about −5° to about 5° C. by high-shear mixing;
    admixing with said suspension a nitrite selected from the group consisting of sodium and potassium nitrite to form nitrous acid in said suspension;
    admixing with said suspension an aqueous solution of an azide selected from the group consisting of sodium, lithium, and potassium azide at a temperature from about 5° to 10° C.;
    high-shear mixing said suspension to maintain turbulent conditions until said suspension reaches room temperature, thereupon formation of diazidoazobenzene being substantially complete;
    isolating diazidoazobenzene;
    forming a suspension of diazidoazobenzene in decalin;
    heating said decalin suspension until nitrogen begins to evolve;
    slowly increasing the temperature of said decalin suspension at a rate from about 0.5° to about 2° C. per minute to a temperature from about 160° C. to about 190° C.;
    continuing to heat said suspension until nitrogen ceases evolving, thereupon formation of dibenzotetrazapentalene being substantially complete;
    isolating dibenzotetrazapentalene;
    forming a suspension of dibenzotetrazapentalene and a concentrated solution of sulfuric acid;
    slowly adding said pentalene-acid suspension to fuming nitric acid at a temperature from about −5° C. to about 5° C.;
    heating said pentalene-acid suspension to a temperature from about 55° to about 65° C. until the formation of tetranitrodibenzo-1,3a,4,6a-tetrazapentalene is complete; and
    isolating tetranitrodibenzo-1,3a,4,6a-tetrazapentalene.

2. The method of claim 1 wherein the temperature of said decalin suspension is increased to a temperature from 175° to 185° C.

3. The method of claim 2 wherein diaminoazobenzene is isolated by the steps comprising:
    filtering said reaction mixture after refluxing has been stopped, thereby removing insoluble lead salts and leaving a red-orange filtrate;
    dissolving said red-orange filtrate in a solvent;
    eluting said filtrate solution on a silica gel column, whereby a red fraction is produced;
    collecting said red fraction; and
    evaporating said solvent, thereby isolating diaminoazobenzene.

4. The method of claim 3 wherein diazidoazobenzene is isolated by filtration at about room temperature.

5. The method of claim 3 wherein dibenzotetrazapentalene is isolated by the steps comprising:
    pouring the contents of said reactor into ice water with a temperature from about 1° C. to about 15° C.; thereby forming an orange-red precipitate; and
    filtering said precipitate, thereby isolating dibenzotetrazapentalene.

6. The method of claim 4 wherein dibenzotetrazapentalene is isolated by the steps comprising:
    pouring the contents of said reactor into ice water with a temperature from about 1° C. to about 15° C.; thereby forming an orange-red precipitate; and
    filtering said precipitate, thereby isolating dibenzotetrazapentalene.

* * * * *